United States Patent [19]

Straub

[11] Patent Number: 5,708,177
[45] Date of Patent: Jan. 13, 1998

[54] PROCESS FOR THE PREPARATION OF OPTICALLY ACTIVE ORTHO-SUBSTITUTED 4-ARYL-DIHYDROPYRIDINES

[75] Inventor: Alexander Straub, Wuppertal, Germany

[73] Assignee: Bayer Aktiengesellschaft, Leverkusen, Germany

[21] Appl. No.: 697,467

[22] Filed: Aug. 26, 1996

[30] Foreign Application Priority Data

Sep. 1, 1995 [DE] Germany .................. 195 32 320.3

[51] Int. Cl.⁶ .................. C07D 211/82; C07D 211/84; C07D 401/04; C07D 409/04
[52] U.S. Cl. .................. 546/257; 546/269.4; 546/280.4; 546/283.7; 546/286; 546/304; 546/326; 546/327
[58] Field of Search ............... 546/257, 269.4, 546/280.4, 283.7, 286, 304, 326, 327

[56] References Cited

U.S. PATENT DOCUMENTS 3,954,737  5/1976  Rinehart, Jr. et al. ............... 260/239.3
4,988,717  1/1991  Wehinger et al. ............... 514/350
5,288,928  2/1994  Broger et al. ............... 568/807
5,374,727  12/1994  Broger ............... 546/95
5,481,008  1/1996  Broger et al. ............... 546/176

FOREIGN PATENT DOCUMENTS 282904  9/1988  European Pat. Off. .
2562540  10/1985  France .

OTHER PUBLICATIONS

S. Goldmann, et al., Angew Chm. Int. Ed. Eng., vol. 30, pp. 1559–1578 (1991).

Database WPI, AN 91–263838, Abstract of JP 03–173869, (1991).

M. Hudlick, "Reductions in Organic Chemistry" pp. 4–24, John Wilegt Sons, New York (1984).

Primary Examiner—Zinna Northington Davis
Attorney, Agent, or Firm—Sprung Kramer Schaefer & Briscoe

[57] ABSTRACT

The invention relates to a process for the preparation of optically active ortho-substituted 4-aryl- or heteroaryl-1,4-dihydropyridines by oxidation and subsequent reduction from their opposite enantiomers.

7 Claims, No Drawings

PROCESS FOR THE PREPARATION OF OPTICALLY ACTIVE ORTHO-SUBSTITUTED 4-ARYL-DIHYDROPYRIDINES

The present invention relates to a process for the preparation of optically active ortho-substituted 4-aryl- or heteroaryl-1,4-dihydropyridines by oxidation and subsequent reduction from their opposite enantiomers.

4-Substituted 1,4-dihydropyridines possess a chiral centre at C-4, if their core unit is substituted unsymmetrically. It is already known that the two enantiomers resulting therefrom can differ fundamentally in their pharmacological activity (cf. EP 26 317 A). Processes to date for the preparation of the desired enantiomer are dependent on the use of chiral auxiliaries. They comprise either enantioselective syntheses or racemate separation via a diastereomer mixture obtained by achiral syntheses. In the latter case, 50% of the "wrong" enantiomer, which is likewise laboriously synthesized, is always obtained, for which there is generally no use.

It is already known that 4-(ortho-aryl)-substituted 1,4-dihydropyridines can occur in two rotameric forms with respect to the 4-aryl radical, the synperiplanar (sp) and the considerably rarer antiperiplanar (ap) form. It is further known that biaryl systems can only form stable atropisomers if they are unsymmetrically ortho-substituted, and free rotation about their bond axis is hindered.

In addition, methods for the oxidation of dihydropyridines to pyridines and specific reductions of pyridines are also known, no knowledge being available, however, on the stereochemical course of such reactions on the corresponding enantiomers.

The invention relates to a combined oxidative/reductive process for the preparation of optically active 1,4-dihydropyridines which have a chiral C atom in the 4 position and are substituted by an aromatic radical which has at least one substituent in the ortho position.

Typical representatives which can be prepared by the process of the invention are, for example, optically active dihydropyridines of the general formula (I) whose chiral C atom in the 4 position carries an ortho-substituted aryl radical

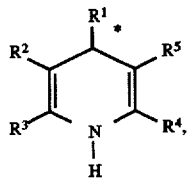

in which $R^1$ represents an aryl radical of the formula

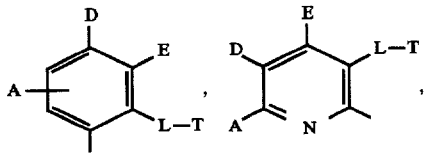

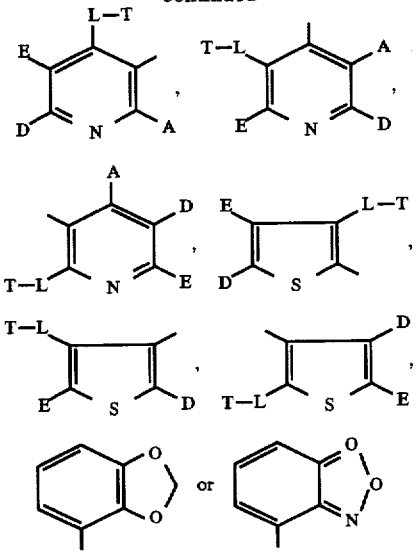

in which

A, D and E are identical or different and denote hydrogen, halogen, cyano, trifluoromethyl or denote straight-chain or branched alkyl or alkenyl having in each case up to 6 carbon atoms, each of which is optionally substituted by aryl having 6 to 10 carbon atoms, by a 5- to 7-membered saturated or unsaturated heterocycle having up to 3 hetero atoms selected from the group consisting of S, N and/or O or by straight-chain or branched alkoxycarbonyl having up to 8 carbon atoms or carboxyl, or denote a group of the formula $-NR^6R^7$, $-OR^8$, $-S(O)_aR^9$, $-SR^{10}$ or $-P(O)(OR^{11})(OR^{12})$, in which $R^6$, $R^7$, $R^8$ and $R^{10}$ are identical or different and denote hydrogen, straight-chain or branched alkyl having up to 8 carbon atoms, benzyl, aryl having 6 to 10 carbon atoms or a 5- to 7-membered saturated or unsaturated heterocycle having up to 3 hetero atoms selected from the group consisting of S, N and/or O, a denotes a number 1 or 2, $R^9$ denotes straight-chain or branched alkyl having up to 6 carbon atoms, benzyl, phenyl or tolyl, $R^{11}$ and $R^{12}$ are identical or different and denote hydrogen or straight-chain or branched alkyl having up to 6 carbon atoms, L denotes a direct bond, a sulphur or oxygen atom or a radical of the formula $-NH$ or $SO_2$, T, depending on the definition of the substituent L, has one of the chemically meaningful meanings given above of A, D and/or E and is identical to or different from this, but in the cases L=bond or $-SO_2$ does not represent hydrogen, or denotes a radical of the formula $-CHF_2$, or D and E, in the directly adjacent case, or E and T, with inclusion of the aromatic double bond, in each case together form a 5- to 8-membered, partially unsaturated or unsaturated carbocycle or heterocycle having up to 3 hetero atoms selected from the group consisting of S, N and/or O, where the ring systems are optionally up to disubstituted identically or differently by halogen, hydroxyl, nitro, cyano, trifluoromethyl, by straight-chain or branched alkyl or alkoxy having in each case up to 6 carbon atoms, by aryl having 6 to 10 carbon atoms or by a 5- to 6-membered aromatic heterocycle having up to 3 hetero atoms selected from the group consisting of S, N and/or O, $R^2$ and $R^5$ are identical or different and represent cyano, nitro, carboxyl or straight-chain or branched alkoxycarbonyl having up to 6 carbon atoms which is optionally substituted by straight-chain or branched alkoxy or acyl having in each case up to 8 carbon atoms or by straight-chain or branched alkyl having up to 6 carbon atoms, which can itself be substituted by straight-chain or branched acyl having up to 4 carbon atoms, pyridyl, furanyl or by a group of the formula $-NR^{13}R^{14}$,
in which
$R^{13}$ and $R^{14}$ are identical or different and denote hydrogen, straight-chain or branched alkyl having up to 6 carbon atoms, aryl having 6 to 10 carbon atoms or benzyl, where the ring systems are optionally substituted by halogen, or
alkoxycarbonyl is optionally substituted by a group of the formula $-NR^{15}R^{16}$,
in which
$R^{15}$ and $R^{16}$ have the meaning cited above of $R^{13}$ and $R^{14}$ and are identical to or different from these, or
$R^2$ and/or $R^5$ represent a radical of the formula $-PO(OR^{17})(OR^{18})$, $-SO_2R^{19}$ or $-CO-NR^{20}R^{21}$,
in which
$R^{17}$ and $R^{18}$ have the meaning given above of $R^{10}$ and $R^{11}$ and are identical to or different from these,
or
$R^{17}$ and $R^{18}$ together form a radical of the formula

$R^{19}$ has the meaning given above of $R^9$ and is identical to or different from this,
$R^{20}$ and $R^{21}$ are identical or different and denote hydrogen, straight-chain or branched alkyl having up to 6 carbon atoms or phenyl, $R^3$ and $R^4$ are identical or different and represent amino, cyano or straight-chain or branched alkinyl or alkyl having in each case up to 4 carbon atoms, each of which is optionally substituted by hydroxyl or by a group of the formula $-(O-CO)_b-NR^{22}R^{23}$,
in which
b denotes a number 0 or 1,
$R^{22}$ and $R^{23}$ are identical or different and have the meaning given above of $R^6$ and $R^7$, or
alkyl is optionally substituted by straight-chain or branched alkoxy having up to 6 carbon atoms which can itself be substituted by a group of the formula $-NR^{24}R^{25}$,
in which
$R^{24}$ and $R^{25}$ have the meaning given above of $R^{13}$ and $R^{14}$ and are identical to or different from these, or
$R^2$ and $R^3$, or $R^4$ and $R^5$, together form a radical of the formula

in which
X denotes an oxygen or sulphur atom or a group of the formula $-NR^{26}$ or $-(CH_2)_c$,
in which
$R^{26}$ denotes hydrogen, phenyl or straight-chain or branched alkyl having up to 4 carbon atoms,
c denotes a number 1, 2 or 3,
and
Y denotes a group of the formula $CO-$, $SO_2-$ or $-SO$.

The process of the invention for the preparation of optically active 1,4-dihydropyridines is characterized in that 1,4-dihydropyridines which have a chiral C atom in the 4-position and are substituted by an ortho-substituted aryl or heteroaryl radical are first converted by oxidation into atropisomeric pyridines and these are then reduced in a second step back to 1,4-dihydropyridines, either an inversion taking place to form the mirror-image isomer or a racemization taking place with partial retention to a differing extent.

A preferred process is to be seen in the fact that optically active 1,4-dihydropyridines of the formula (I) which have a chiral C atom in the 4-position and are substituted by an ortho-substituted aryl radical and which are present in the synperiplanar (sp) form (Ia) or antiperiplanar (ap) form (Ib) or their antipodes,

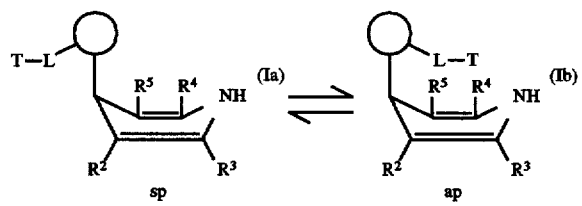

in which
$R^2$, $R^3$, $R^4$, $R^5$, L and T have the meaning given above
and

includes the ortho-substituted aromatic ring systems cited above under the substituent $R^1$, are first convened by oxidation into the atropisomeric pyridines of the general formulae (IIa) or (IIb)

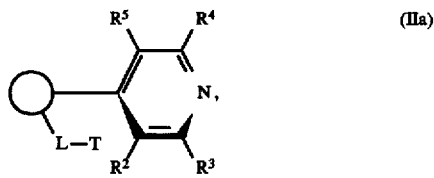

-continued

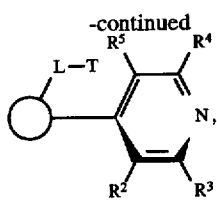

(IIb)

in which $R^2$, $R^3$, $R^4$, $R^5$, L, T and

have the meaning given above, and, in a second step, these pyridines are reduced back to 1,4-dihydropyridines of the formula (I), either an inversion taking place to form the mirror-image isomer or a racemization taking place with partial retention to a differing extent.

The process of the invention can be described by way of example by the following formula scheme:

mirror-image enantiomers are obtained without any chiral auxiliary in an elegant manner and with very high enantiomeric purity and yield. Furthermore, it is possible in other cases to racemize the undesired enantiomer and thus obtain half of the desired enantiomer.

A further advantage of the process of the invention, in particular with regard to the cost factor, is also due to the fact that, in contrast to the many-stage and frequently highly expensive enantioselective chemical syntheses or separation methods, the entire reaction sequence is very short and not very complex.

Surprisingly, it has also been found that, by suitable choice of oxidizing agent, a change in the atropisomer ratio is obtained favouring the atropisomeric pyridine produced from the sp-rotamer 1,4-DHP and necessary for an inversion.

It has further been found that the reduction of the atropisomeric pyridines proceeds with high enantioselectivity to give the corresponding 4-ortho-substituted aryl- or heteroaryl- 1,4-dihydropyridines.

Heterocycle, in the context of the invention, generally represents a saturated or unsaturated 5- to 8-membered, preferably 5- to 6-membered, heterocycle, which can con-

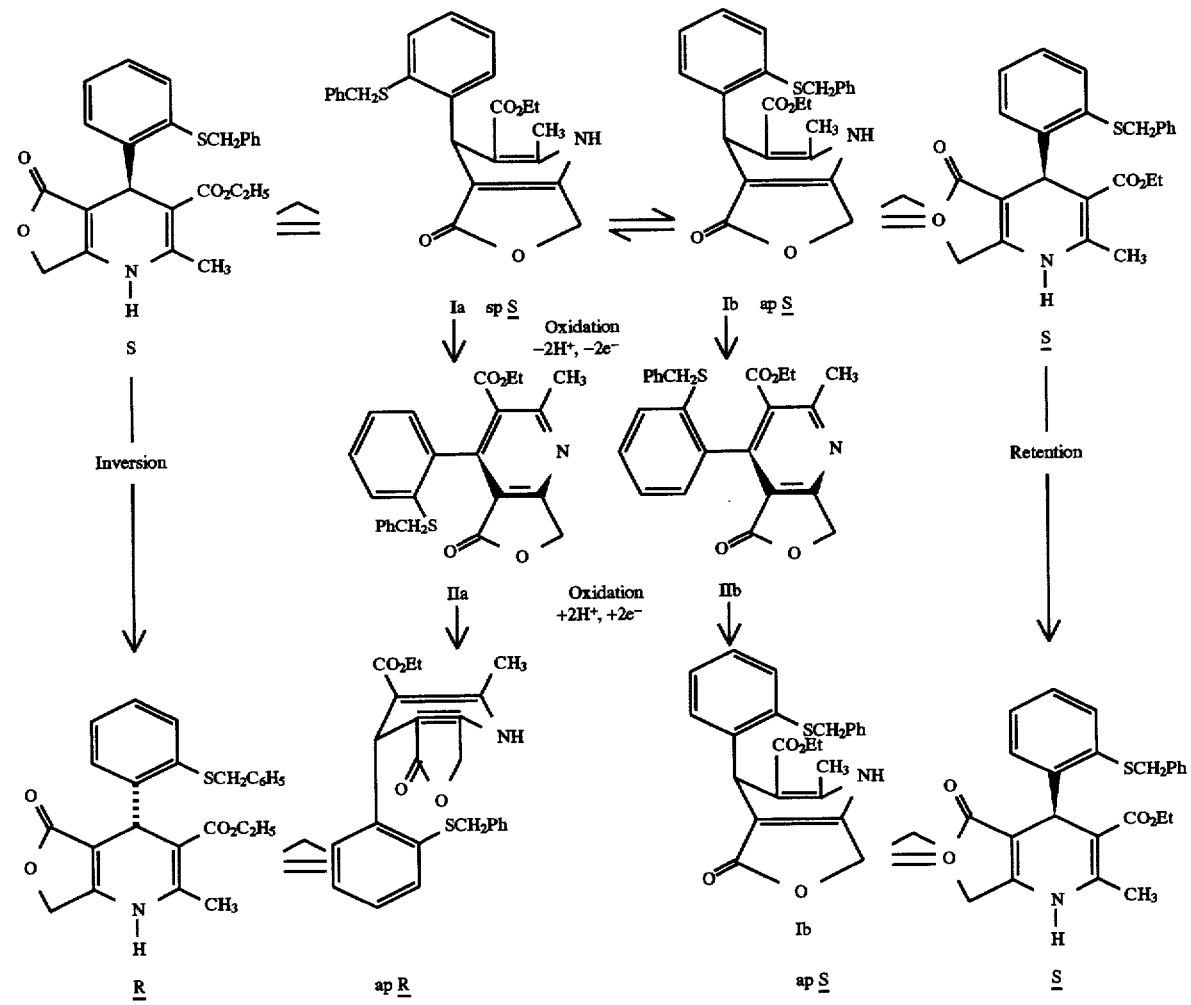

Surprisingly, when the process of the invention is carried out starting from the undesired 4-ortho-substituted aryl- or heteroaryl-1,4-dihydropyridine enantiomers, their desired tain up to 3 hetero atoms selected from the group consisting of S, N and/or O. Those which may be mentioned by way of example are: pyridyl, thienyl, furyl, pyrrolyl, thiazolyl, oxazolyl, imidazolyl, morpholinyl or piperidyl. Preference is given to pyridyl and thienyl.

Oxidizing agents which are suitable, depending on the 1,4-dihydropyridines to be reacted, are heterogeneous (also using support materials, such as montmorillonite) and homogeneous systems, anodic oxidations, enzymatic oxidations, eg. by P450 oxidase and catalase, $S_8$, $NO_x$ (x=1, 2), $CrO_3$, $O_2$, $KMNO_4/HAc$, Pd/C, chloranil, DDQ, p-nitrosodimethylaniline, $H_2O_2$, $AgNO_3$, diisoamyl disulphide, Pt/HAc, $HgAc_2$, $I_2$, iodosobenzene, iron carbonyls or nickel carbonyls, $PbO_2$, benzoquinone, $NaNO_2$ in acidic solvents, $HNO_3$, $HNO_2$, $Fe(NO_3)_3$, $Cu(NO_3)_2$, $Br_2$/NaOAc, $KMnO_4$, $Ba(MnO_4)_2$, $MnO_2$, DBU, $HClO_4$, nitrobenzene, $K_3[Fe(CN)_6]/K_2CO_3$, methyl acridinium salts, cerium ammonium nitrate, nitrosonium salts such as $NOBF_4$, nitronium salts such as $NO_2BF_4$, peracids such as m-chloroperbenzoic acid, $NaIO_4$, oxones or dimethyldioxirane. Preference is given to NO, $HNO_3$, $NOBF_4$, $NO_2BF_4$ and anodic oxidations.

Solvents for the oxidations which are suitable are generally inert solvents which do not change under the reaction conditions. These include, for example, acetonitrile, hydrochloric acid, acetic acid, sulphuric acid, nitric acid, DMF, water, benzene, DMSO, chloroaniline, acetone, glacial acetic acid, ethers such as dioxane, diethyl ether, diisopropyl ether or tetrahydrofuran, or chlorinated hydrocarbons, such as dichloromethane, chloroform or carbon tetrachloride. It is equally possible to use mixtures of the abovementioned solvents and/or water. Preference is given to chloroform, glacial acetic acid, acetone, dioxane, acetonitrile, dichloromethane or carbon tetrachloride.

The reaction temperatures can be varied in a relatively wide range. Generally, temperatures between –60° C. and +200° C. are employed, preferably between 0° C. and +100° C.

If appropriate, the oxidation is also carried out under a protective gas atmosphere.

The reductions are generally carried out by reducing agents, such as $NaBH_4$, $BH_3$, $LiAlH_4$, sodium dithionite or by cathodic reductions in a conventional electrolysis cell comprising cathode, anode and reference electrode in solution, if appropriate with addition of a supporting electrolyte. The cell can be divided by a membrane into cathode chamber and anode chamber or be undivided, the above-described oxidation of the DHP being able to proceed at the same time at the anode.

Cathode materials which are suitable are generally the materials conventional in electrochemistry. Preference is given to the mercury pool electrode, graphite, carbon, Pt, Pd, Pb, Cd or Ni.

Anode materials which are suitable are likewise the conventional materials, Pd, carbon or graphite being preferred.

Supporting electrolytes used in the context of the invention are quaternary ammonium, alkali metal and alkaline earth salts. Preference is given to the corresponding halides, perchlorates, tetrafluoroborates, hexafluoroplatinates, sulphates or phosphates.

Solvents which are suitable are generally protic and aprotic solvents and their mixtures, such as acetonitrile, HMPT, DMSO, DMF, water, buffer solutions of phosphate salts, acetate salts or citrate salts, dimethylacetamide, N-methylpyrroilidone, sulpholane, dichloromethane and acetone.

The cathodic reduction is generally carried out under voltage control between –0.5 V and –2.5 V, preferably –1 V and –1.9 V, or under current control at currents of 5 mA to 1 A, preferably 10 mA to 500 mA. It can, if appropriate, be carried out under a protective gas atmosphere.

Preferably, dihydropyridines of the general formula (I) are prepared by the process of the invention, in which $R^1$ represents a radical of the formula

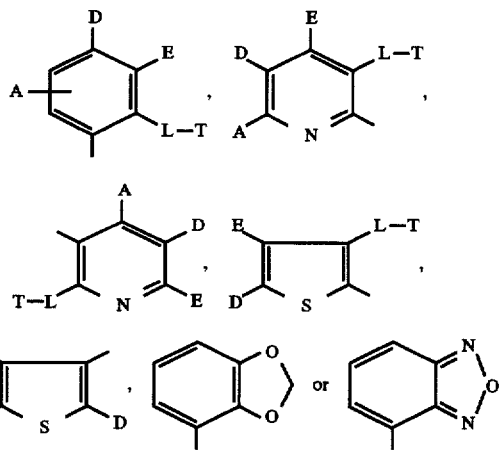

in which

A, D and E are identical or different and denote hydrogen, fluorine, chlorine, bromine, cyano, trifluoromethyl or straight-chain or branched alkyl or alkenyl having in each case up to 5 carbon atoms, each of which is optionally substituted by phenyl, naphthyl, pyridyl or by straight-chain or branched alkoxycarbonyl having up to 6 carbon atoms or carboxyl, or denote a group of the formula $-NR^6R^7$, $-OR^8$, $-S(O)_aR^9$, $-SR^{10}$ or $-P(O)(OR^{11})(OR^{12})$, in which $R^6$, $R^7$, $R^8$ and $R^{10}$ are identical or different and denote hydrogen, straight-chain or branched alkyl having up to 6 carbon atoms, benzyl, phenyl, pyridyl, furyl or thienyl, a denotes a number 1 or 2, $R^9$ denotes straight-chain or branched alkyl having up to 4 carbon atoms, benzyl, phenyl or tolyl, $R^{11}$ and $R^{12}$ are identical or different and denote hydrogen or straight-chain or branched alkyl having up to 3 carbon atoms, L denotes a direct bond, a sulphur atom or oxygen atom or a radical of the formula —NH or $SO_2$, T, depending on the definition of the substituent L, has one of the chemically meaningful meanings given above of A, D and/or E and is identical to or different from this, but in the cases L=bond or $-SO_2$ does not represent hydrogen, or denotes a radical of the formula $-CHF_2$, or D and E, in the directly adjacent case, or E and T, with inclusion of the aromatic double bond, in each case together form a fused cyclopentenyl, cyclohexenyl, cycloheptenyl, cyclohexadienyl, cycloheptadienyl or pyridyl ring, where the ring systems are optionally substituted by phenyl, thienyl, straight-chain or branched alkyl having up to 4 carbon atoms or pyridyl, $R^2$ and $R^5$ are identical or different and represent cyano, nitro, carboxyl or straight-chain or branched alkoxycarbonyl having up to 5 carbon atoms which is optionally substituted by straight-chain or branched alkoxy or acyl having in each case up to 6 carbon atoms or by straight-chain or branched alkyl having up to 5 carbon atoms, which can itself be substituted by straight-chain or branched acyl having up to 3 carbon atoms, pyridyl, furanyl or by a group of the formula —$NR^{13}R^{14}$, in which $R^{13}$ and $R^{14}$ are identical or different and denote hydrogen, straight-chain or branched alkyl having up to 5 carbon atoms, phenyl, naphthyl or benzyl, where the ring systems are optionally substituted by fluorine, chlorine or bromine, or alkoxycarbonyl is optionally substituted by a group of the formula —$NR^{15}R^{16}$, in which $R^{15}$ and $R^{16}$ have the meaning cited above of $R^{13}$ and $R^{14}$ and are identical to or different from these, or $R^2$ and/or $R^5$ represent a radical of the formula —PO($OR^{17}$)($OR^{18}$), —$SO_2R^{19}$ or —CO—$NR^{20}R^{21}$, in which $R^{17}$ and $R^{18}$ have the meaning given above of $R^{10}$ and $R^{11}$ and are identical to or different from these, or $R^{17}$ and $R^{18}$ together form a radical of the formula

$R^{19}$ has the meaning given above of $R^9$ and is identical to or different from this, $R^{20}$ and $R^{21}$ are identical or different and denote hydrogen, straight-chain or branched alkyl having up to 4 carbon atoms, or phenyl, $R^3$ and $R^4$ are identical or different and represent amino, cyano or straight-chain or branched alkinyl or alkyl having in each case up to 3 carbon atoms, which is optionally substituted by hydroxyl or by a group of the formula —(O—CO)$_b$—$NR^{22}R^{23}$, in which b denotes a number 0 or 1, $R^{22}$ and $R^{23}$ are identical or different and have the meaning given above of $R^6$ and $R^7$, or alkyl is optionally substituted by straight-chain or branched alkoxy having up to 4 carbon atoms which can itself be substituted by a group of the formula —$NR^{24}R^{25}$, in which $R^{24}$ and $R^{25}$ have the meaning given above of $R^{13}$ and $R^{14}$ and are identical to or different from this, or $R^2$ and $R^3$, or $R^4$ and $R^5$, together form a radical of the formula

in which

X denotes an oxygen atom or sulphur atom or a group of the formula —$NR^{26}$ or —(CH$_2$)$_c$, in which $R^{26}$ denotes hydrogen, phenyl or straight-chain or branched alkyl having up to 3 carbon atoms, c denotes a number 1, 2 or 3, and Y denotes a group of the formula CO—, SO$_2$— or —SO.

Particularly preferably, compounds of the general formula (I) are prepared by the process of the invention, in which $R^1$ represents a radical of the formula

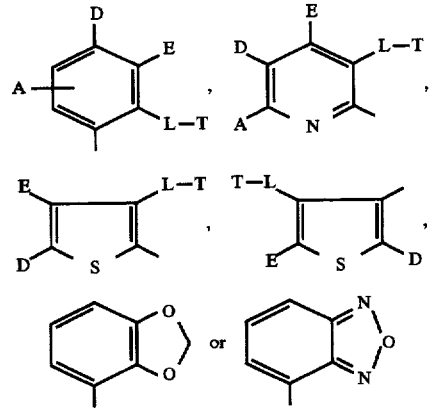

in which

A, D and E are identical or different and denote hydrogen, fluorine, chlorine, bromine, cyano, trifluoromethyl or straight-chain or branched alkyl or alkenyl having in each case up to 4 carbon atoms each of which is optionally substituted by phenyl, naphthyl, pyridyl or by straight-chain or branched alkoxycarbonyl having up to 5 carbon atoms or carboxyl, or denote a group of the formula —$NR^6R^7$, —$OR^8$, —$S(O)_aR^9$, —$SR^{10}$ or —$P(O)(OR^{11})(OR^{12})$, in which $R^6$, $R^7$, $R^8$ or $R^{10}$ are identical or different and denote hydrogen, straight-chain or branched alkyl having up to 4 carbon atoms, benzyl, phenyl, pyridyl or furyl, a denotes a number 1 or 2, $R^9$ denotes methyl, benzyl, phenyl or tolyl, $R^{11}$ and $R^{12}$ are identical or different and denote hydrogen or straight-chain or branched alkyl having up to 3 carbon atoms, L denotes a direct bond, a sulphur atom or oxygen atom or a radical of the formula —NH or SO$_2$, T, depending on the definition of the substituent L, has one of the chemically meaningful meanings given above of A, D and/or E and is identical to or different from this, but in the cases L=bond or —SO$_2$ does not represent hydrogen, or denotes a radical of the formula —CHF$_2$, or D and E, in the directly adjacent case, or E and T, with inclusion of the aromatic double bond, in each case together form a fused cyclopentenyl, cyclohexenyl, cycloheptenyl, cyclohexadienyl, cycloheptadienyl or pyridyl ring, where the ring systems are optionally substituted by phenyl, thienyl, straight-chain or branched alkyl having up to 3 carbon atoms or pyridyl, $R^2$ and $R^5$ are identical or different and denote cyano, nitro, carboxyl or straight-chain or branched alkoxycarbonyl having up to 4 carbon atoms which is optionally substituted by straight-chain or branched alkoxy or acyl having in each case up to 3 carbon atoms or by straight-chain or branched alkyl having up to 3 carbon atoms, which can itself be substituted by straight-chain or branched acyl having up to 3 carbon atoms, pyridyl, furanyl or by a group of the formula —NR$^{13}$R$^{14}$, in which $R^{13}$ and $R^{14}$ are identical or different and denote hydrogen or straight-chain or branched alkyl having up to 4 carbon atoms, or $R^2$ and/or $R^5$ represent a radical of the formula —PO(OR$^{17}$)(OR$^{18}$), —SO$_2$R$^{19}$ or —CO—NR$^{20}$R$^{21}$, in which $R^{17}$ and $R^{18}$ have the meaning given above of $R^{10}$ and $R^{11}$ and are identical to or different from these, or $R^{17}$ and $R^{18}$ together form a radical of the formula

$R^{19}$ has the meaning given above of $R^9$ and is identical to or different from this, $R^{20}$ and $R^{21}$ are identical or different and denote hydrogen, straight-chain or branched alkyl having up to 3 carbon atoms, $R^3$ and $R^4$ are identical or different and represent amino, cyano or straight-chain or branched alkinyl or alkyl having in each case up to 3 carbon atoms, which is optionally substituted by hydroxyl or by a group of the formula —(O—CO)$_b$—NR$^{22}$R$^{23}$, in which b denotes a number 0 or 1, $R^{22}$ and $R^{23}$ are identical or different and have the meaning given above of $R^6$ and $R^7$, or alkyl is optionally substituted by straight-chain or branched alkoxy having up to 3 carbon atoms which can itself be substituted by a group of the formula —NR$^{24}$R$^{25}$, in which $R^{24}$ and $R^{25}$ have the meaning given above of $R^{13}$ and $R^{14}$ and are identical to or different from this, or $R^2$ and $R^3$, or $R^4$ and $R^5$, together form a radical of the formula

in which

X denotes an oxygen atom or sulphur atom or a group of the formula —NR$^{26}$ or —(CH$_2$)$_c$, in which $R^{26}$ denotes hydrogen, phenyl or straight-chain or branched alkyl having up to 3 carbon atoms, c denotes a number 1, 2 or 3, and Y denotes the CO group.

The process of the invention enables in an elegant manner the conversion of undesired 4-ortho-substituted aryl- or heteroaryl-1,4-dihydropyridine enantiomers into the corresponding mirror-image enantiomers of the general formula (I), which are valuable pharmaceuticals.

EXPERIMENTAL PART

The preparative electrochemistry was carried out using a Stanford Wenking Potentiostat ST 72. The reaction vessel used was an electrolysis cell divided by a diaphragma into an anode compartment and cathode compartment. For reductions, a mercury pool electrode was used. The mercury used was washed with methanol after each reaction in a separating funnel and reused. The reference electrode used was a saturated calomel electrode, which was coupled via a Luggin capillary to the cathode compartment. The anode used, and in the case of oxidations, also the cathode, was a platinum sheet electrode. The cell was thermostated at 20° C. and operated in an argon atmosphere. "Manganese dioxide, precipitated active, for synthesis", Article No. 805958, Merck Schuchardt, was used for the oxidation of the DHPs.

EXAMPLE 1

Oxidation of (−)-ethyl 2-methyl-4-(2-benzylthiophenyl)-5-oxo-1,4,5,7-tetrahydro-furo[3,4-b]pyridine-3-carboxylate to (+)-ethyl 2-methyl-4-(2-benzylthiophenyl)-5-oxo-5,7-dihydrofuro[3,4-b]pyridine-3-carboxylate with MnO$_2$

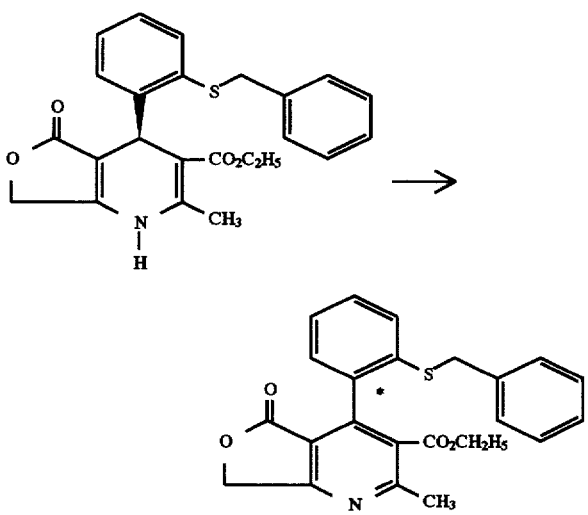

1.37 g (3.3 mmol) of (−)-ethyl 2-methyl-4-(2-benzylthiophenyl)-5-oxo-1,4,5,7-tetrahydrofuro[3,4-b]pyridine-3-carboxylate are dissolved in 150 ml of chloroform and, after addition of 5.73 g of MnO$_2$, are sonicated in an ultrasonic bath. After filtering off by suction over kieselguhr and evaporation of the solvent in vacuo, 1.2 g (87% of theory) of (+)-ethyl 2-methyl-4-(2-benzylthiophenyl)-5-oxo-5,7-dihydrofuro[3,4-b]pyridine-3-carboxylate are obtained.

$[\alpha]^{20}_D$=51.35° (c=0.56, CHCl$_3$) HPLC: atropisomer 2 in the elution sequence MS (EI): 419 (M$^+$, 15%), 91 (100%)

EXAMPLE 2

Oxidation of (−)-ethyl 2-methyl-4-(2-benzylthiophenyl)-5-oxo-1,4,5,7-tetrahydrofuro[3,4-b]pyridine-3-carboxylate with K$_3$(Fe(CN)$_6$)

50 mg (0.12 mmol) of (−)-ethyl 2-methyl-4-(2-benzylthiophenyl)-5-oxo-1,4,5,7-tetrahydrofuro[3,4-b]pyridine-3-carboxylate in 3 ml of acetonitrile are admixed with 1 g of K$_3$(Fe(CN)$_6$) in 4 ml of water and, after addition of a spatula tip of $K_2CO_3$, the mixture is stirred overnight at room temperature under an argon atmosphere. After addition of 1 g of $K_3(Fe(CN)_6)$ and 200 mg of $K_2CO_3$, the mixture is further stirred for 1 h, then poured into 50 ml of water, extracted with ethyl acetate and chromatographed on silica gel (toluene→toluene/ethyl acetate=5:1).

Yield: 4 mg (8% of theory)

EXAMPLE 3

Oxidation of (−)-ethyl 2-methyl-4-(2-benzylthiophenyl)-5-oxo-1,4,5,7-tetrahydrofuro[3,4-b]pyridine-3-carboxylate with cerium(IV) ammonium nitrate A solution of 0.15 g of cerium(IV)ammonium nitrate in 1 ml of water is added dropwise under an argon atmosphere to 40 mg (0.1 mmol) of (−)-ethyl 2-methyl-4-(2-benzylthiophenyl)-5-oxo-1,4,5,7-tetrahydrofuro[3,4-b] pyridine-3-carboxylate in 8 ml of acetone. The mixture is stirred for 3 h at room temperature, poured into water, extracted with ethyl acetate and the ee of the residue remaining after removal of the solvent in vacuo is determined by chiral HPLC.

EXAMPLE 4

Oxidation of (−)-ethyl 2-methyl-4-(2-benzylthiophenyl)-5-oxo-1,4,5,7-tetrahydrofuro[3,4-b]pyridine-3-carboxylate with chloranil A mixture of 40 mg (0.1 mmol) of (−)-ethyl 2-methyl-4-(2-benzylthiophenyl)-5-oxo-1,4,5,7-tetrahydrofuro[3,4-b] pyridine-3-carboxylate, 21 mg of chloranil and 5 ml of toluene is boiled overnight in an argon atmosphere. After the mixture is washed with water and extracted with ethyl acetate, the ee is determined.

EXAMPLE 5

Oxidation of (−)-ethyl 2-methyl-4-(2-benzylthiophenyl)-5-oxo-1,4,5,7-tetrahydrofuro[3,4-b]pyridine-3-carboxylate at the platinum anode 100 mg (0.24 mmol) of (−)-ethyl 2-methyl-4-(2-benzylthiophenyl)-5-oxo-1,4,5,7-tetrahydrofuro[3,4-b] pyridine-3-carboxylate together with 0.7 g of $TEABF_4$ as supporting electrolyte, in 35 ml of acetonitrile, are introduced into the anode compartment of a divided membrane cell. The cathode compartment comprised the substrate-free electrolyte. Electrolysis is carried out at approximately 30 mA and the reaction is controlled by thin-layer chromatography, in the course of which reaction an intermediate occurs. After the reaction was completed, the product was precipitated in water, filtered off by suction and chromatographed on silica gel.

Yield: 52 mg (52%).

$R_f(SiO_2$, toluene/ethyl acetate=1:1): (−)-ethyl 2-methyl-4-(2-benzylthiophenyl)-5-oxo-1,4,5,7-tetrahydrofuro[3,4-b] pyridine-3-carboxylate: 0.18 (+)-ethyl 2-methyl-4-(2-benzylthiophenyl)-5-oxo-5,7-dihydrofuro[3,4-b]pyridine-3-carboxylate: 0.54

EXAMPLE 6

Oxidation of (−)-ethyl 2-methyl-4-(2-benzylthiophenyl)-5-oxo-1,4,5,7-tetrahydrofuro[3,4-b]pyridine-3-carboxylate with $NOBF_4$ or $NO_2BF_4$ 20 mg (0.05 mmol) of (−)-ethyl 2-methyl-4-(2-benzylthiophenyl)-5-oxo-1,4,5,7-tetrahydrofuro[3,4-b] pyridine-3-carboxylate, in 1 ml of acetonitrile, are admixed with a solution of 6 mg of $NOBF_4$ (or $NO_2BF_4$) in 1 ml of acetonitrile. The batch turns light yellow and is quantitatively reacted within the course of 20 min. After rotary evaporation, the product is stirred with aqueous $NaHCO_3$ solution and extracted with ethyl acetate.

EXAMPLE 7

Oxidation of (−)-ethyl 2-methyl-4-(2-benzylthiophenyl)-5-oxo-1,4,5,7-tetrahydrofuro[3,4-b]pyridine-3-carboxylate with concentrated $HNO_3$ 100 mg (0.24 mmol) of (−)-ethyl 2-methyl-4-(2-benzylthiophenyl)-5-oxo-1,4,5,7-tetrahydrofuro[3,4-b] pyridine-3-carboxylate are introduced into 10 ml of chloroform and are vigorously stirred after addition of 3 ml of 65 percent strength $HNO_3$. After 2 min, the mixture is poured into 100 ml of water, neutralized with $K_2CO_3$, extracted with chloroform, dried with $MgSO_4$ and concentrated in vacuo. After chromatography on silica gel using toluene as eluent, 40 mg (40% of theory) of the pyridine compound are obtained, whose ee is determined in chiral HPLC.

EXAMPLE 8

Oxidation of (−)-ethyl 2-methyl-4(2-benzylthiophenyl)-5-oxo-1,4,5,7-tetrahydrofuro[3,4-b]pyridine-3-carboxylate with N-methylacridinium iodide A solution of 300 mg (0.71 mmol) of (−)-ethyl 2-methyl-4-(2-benzylthiophenyl)-5-oxo-1,4,5,7-tetrahydrofuro[3,4-b] pyridine-3-carboxylate, 800 mg (2.49 mmol) of N-methylacridinium iodide, 150 ml of acetonitrile and 1.6 ml of $2N H_2SO_4$ is refluxed overnight in an argon atmosphere. After cooling, any precipitate settled is filtered off by suction and the solution, after treatment with aqueous $NaHCO_3$ solution, is extracted with ethyl acetate, concentrated by evaporation and chromatographed.

Yield: 96 mg (32% of theory)

EXAMPLE 9

Oxidation of (−)-ethyl 2-methyl-4-(2-benzylthiophenyl)-5-oxo-1,4,5,7-tetrahydrofuro[3,4-b]pyridine-3-carboxylate with $NaNO_2/HCl$ in ether or $CHCl_3$ In a narrow glass vessel, 0.74 g of $NaNO_2$ is overlaid with 10 ml of ether and 1 ml of half-concentrated HCl is slowly added. 1 ml of the ether phase of this solution is immediately added to a solution of 36 mg (0.085 mmol) of (−)-ethyl 2-methyl-4-(2-benzylthiophenyl)-5-oxo-1,4,5,7-tetrahydrofuro[3,4-b]pyridine-3-carboxylate in 2 ml of dioxane or of 30 mg (0.07 mmol) of (−)-ethyl 2-methyl-4-(2-benzyl-thiophenyl)-5-oxo-1,4,5,7-tetrahydrofuro[3,4-b] pyridine-3-carboxylate in 3 ml of $CHCl_3$. The reaction times are 30 min in the first case and 4 min in the second. $K_2HPO_4$ buffer is then added, the organic phase is separated off and chromatographed on a small column.

EXAMPLE 10

Oxidation of (−)-ethyl 2-methyl-4-(2-benzylthiophenyl)-5-oxo-1,4,5,7-tetrahydrofuro[3,4-b]pyridine-3-carboxylate with $NaNO_2/HCl$ in dioxane 40 mg (0.095 mmol) of (−)-ethyl 2-methyl-4-(2-benzylthiophenyl)-5-oxo-1,4,5,7-tetrahydrofuro[3,4-b]

pyridine-3-carboxylate are dissolved in 1 ml of dioxane and 0.56 ml of 10 percent strength HCl and a solution of 16.8 mg of $NaNO_2$ in 0.1 ml of water is added. The mixture is neutralized after 8 h and extracted with ethyl acetate.

EXAMPLE 11

Oxidation of (–)-ethyl 2-methyl-4-(2-benzylthiophenyl)-5-oxo-1,4,5,7-tetrahydrofuro[3,4-b]pyridine-3-carboxylate with $Cu_4(NO_3)_2$ on montmorillonite 30 mg of (–)-ethyl 2-methyl-4-(2-benzylthiophenyl)-5-oxo-1,4,5,7-tetrahydrofuro[3,4-b]pyridine-3-carboxylate are dissolved in 0.6 ml of chloroform and, after addition of 40 mg of $Cu_4(NO_3)_2$ on montmorillonite (Fluka) (1.7 mmol/g), the mixture is kept in an ultrasonic bath for 8 min. After filtering off by suction, rotary evaporation and chromatography, the ee is determined.

EXAMPLE 12

Oxidation of (–)-ethyl 2-methyl-4-(2-benzylthiophenyl)-5-oxo-1,4,5,7-tetrahydrofuro[3,4-b]pyridine-3-carboxylate with $NaNO_2$ in glacial acetic acid 0.5 g of (–)-ethyl 2-methyl-4-(2-benzylthiophenyl)-5-oxo-1,4,5,7-tetrahydro-furo[3,4-b]pyridine-3-carboxylate are dissolved in 15 ml of glacial acetic acid. In the course of 10 min, 0.5 g of $NaNO_2$ is added to the solution which is situated in an 18×180 mm test tube, nitrous gases bubbling through the solution. The batch is then immediately poured into a solution of 25 g of $K_2HPO_4$ in 50 ml of water, stirred, extracted with ethyl acetate and chromatographed on silica gel. 418 mg (84% of theory) of (+)-ethyl 2-methyl-4-(2-benzylthiophenyl)-5-oxo-5,7-dihydrofuro[3,4-b]pyridine-3-carboxylate are obtained.

EXAMPLE 13

Oxidation of (–)-ethyl 2-methyl-4-(2-benzylthiophenyl)-5-oxo-1,4,5,7-tetrahydrofuro[3,4-b]pyridine-3-carboxylate with dilute $HNO_3$ 100 mg (0.24 mmol) of (–)-ethyl 2-methyl-4-(2-benzylthiophenyl)-5-oxo-1,4,5,7-tetrahydrofuro[3,4-b]pyridine-3-carboxylate are introduced into 10 ml of chloroform, 4 ml of 3N $HNO_3$ are added and the mixture is boiled with vigorous stirring until TLC indicates complete reaction.

EXAMPLE 14

Oxidation of (–)-ethyl 2-methyl-4-(2-benzylthiophenyl)-5-oxo-1,4,5,7-tetrahydrofuro[3,4-b]pyridine-3-carboxylate with $KMnO_4$ 40 mg (0.095 mmol) of (–)-ethyl 2-methyl-4-(2-benzylthiophenyl)-5-oxo-1,4,5,7-tetrahydrofuro[3,4-b]pyridine-3-carboxylate, 16 mg of $KMnO_4$ and 35 mg of montmorillonite KSF are taken up in 0.8 ml of $CH_2Cl_2$ and 0.5 ml of water (version 1) or in 3 ml of benzene (version 2). In the first case, the reaction is completed after sonicating for 2 hours with ultrasound, in the second case, sonication is carried out for 1.5 h, 37 mg of $KMnO_4$ and 74 mg of montmorillonite KSF are further added and the mixture is sonicated for a further 3 h. For work-up, the organic phases are separated off and chromatographed on silica gel.

EXAMPLE 15

Oxidation of (–)-isopropyl 2-methyl-4-(2-methylphenyl)-5-oxo-1,4,5,7-tetrahydrofuro[3,4-b]pyridine-3-carboxylate to isopropyl 2-methyl-4(2-methylphenyl)-5-oxo-5,7-dihydrofuro[3,4-b]pyridine-3-carboxylate with manganese dioxide

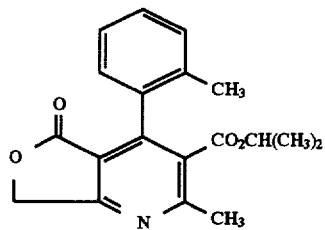

1.1 g (3.36 mmol) of (–)-isopropyl 2-methyl-4-(2-methylphenyl)-5-oxo-1,4,5,7-tetrahydrofuro[3,4-b]pyridine-3-carboxylate are dissolved in 80 ml of chloroform, 5.5 g of $MnO_2$ are added and the mixture is sonicated for 15 min in an ultrasonic bath. The mixture is filtered off with suction over kieselguhr and 1 g (91.5% of theory) of white crystals is obtained.

EXAMPLE 16

Oxidation of (–)-isopropyl 2-methyl-4-(2-methylphenyl)-5-oxo-1,4,5,7-tetrahydrofuro[3,4-b]pyridine-3-carboxylate to isopropyl 2-methyl-4-(2-methylphenyl)-5-oxo-5,7-dihydrofuro[3,4-b]pyridine-3-carboxylate with $NaNO_2$ in glacial acetic acid 50 mg (0.15 mmol) of (–)-isopropyl 2-methyl-4-(2-methylphenyl)-5-oxo-1,4,5,7-tetrahydrofuro[3,4-b]pyridine-3-carboxylate are dissolved in 1.5 ml of glacial acetic acid and 50 mg of sodium nitrite are added in the course of 20 min. The batch is then poured into a solution of 2.7 g of $K_2HPO_4$ in 5 ml of water, shaken with ethyl acetate and chromatographed on silica gel with toluene/ethyl acetate mixtures.

EXAMPLE 17

Cathodic reduction of (+)-ethyl 2-methyl-4-(2-benzylthiophenyl)-5-oxo-5,7-dihydrofuro[3,4-b]pyridine-3-carboxylate to (–)-ethyl 2-methyl-4-(2-benzylthiophenyl)-5-oxo-1,4,5,7-tetrahydrofuro[3,4-b]pyridine-3-carboxylate (S)

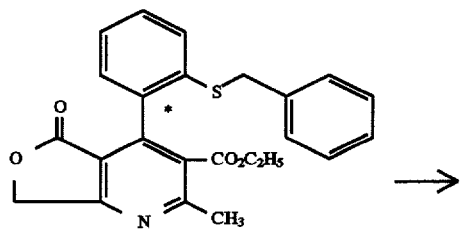

-continued

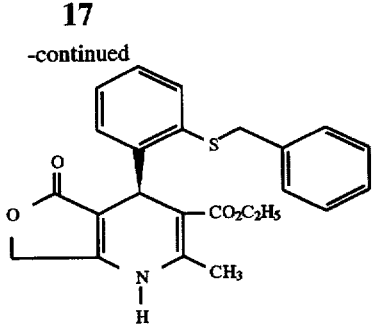

A divided cell having an Hg-pool-cathode, platinum anode and calomel reference electrode is charged with a solution of 120 mg of (+)-ethyl 2-methyl-4-(2-benzylthiophenyl)-5-oxo-5,7-dihydrofuro[3,4-b]pyridine-3-carboxylate and 500 mg of $TBABF_4$ in 50 ml of methanol as catholyte and without substrate as anolyte. Electrolysis is carried out with control of current at 10–20 mA. The reaction was terminated after 2.5 h, since starting material could no longer be observed by thin-layer chromatography. The methanol solution in the cathode compartment was partially evaporated in a rotary evaporator, poured into water and the precipitate filtered off by suction; dissolved in a sparing amount of toluene, it was applied to a column and chromatographed on silica gel with toluene→toluene/ethyl acetate=6:1 gradient. The yield is 45 mg of ethyl 2-methyl-4-(2-benzylthiophenyl)-5-oxo-1,4,5,7-tetrahydrofuro[3,4-b]pyridine-3-carboxylate (38% of theory) having an enantiomer ratio of 90.2:9.8.

$R_f(SiO_2$, toluene/ethyl acetate=1:1): (−)-ethyl 2-methyl-4-(2-benzylthio-phenyl)-5-oxo-1,4,5,7-tetrahydrofuro[3,4-b]pyridine-3-carboxylate: 0.45 chiral HPLC: ee=80.4% (enantiomer 1 in the elution sequence)

EXAMPLE 18

Cathodic reduction of (−)-isopropyl 2-methoxyethyl 4-(2-chloro-3-cyanophenyl)-2,6-dimethylpyridine-3,5-dicarboxylate to isopropyl 2-methoxyethyl 4-(2-chloro-3-cyanophenyl)-2,6-dimethyl-1,4-dihydropyridine-3,5-dicarboxylate

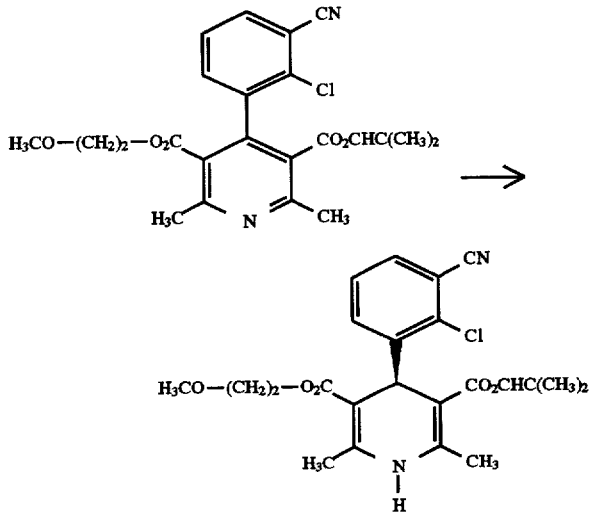

The procedure as described for Example 17 is followed. Starting from 120 mg of (−)-isopropyl 2-methoxyethyl 4-(2-chloro-3-cyanophenyl)-2,6-dimethylpyridine-3,5-dicarboxylate (atropisomer ratio in the elution sequence from chiral HPLC 98: 2; $[\alpha]^{20}_D$=7.2 (c=0.9, MeOH)), after electrolysis at 10–40 mA, 80 mg (67% of theory) of isopropyl 2-methoxyethyl 4-(2-chloro-3-cyanophenyl)-2,6-dimethyl-1,4-dihydropyridine-3,5-dicarboxylate are obtained in the enantiomer ratio 61.3:38.7.

EXAMPLE 19

Cathodic reduction of isopropyl 2-methyl-4-(2-methylphenyl)-5-oxo-5,7-dihydrofuro-[3,4-b]pyridine-3-carboxylate to isopropyl 2-methyl-4-(2-methylphenyl)-5-oxo-1,4,5,7-tetrahydrofuro[3,4-b]pyridine-3-carboxylate

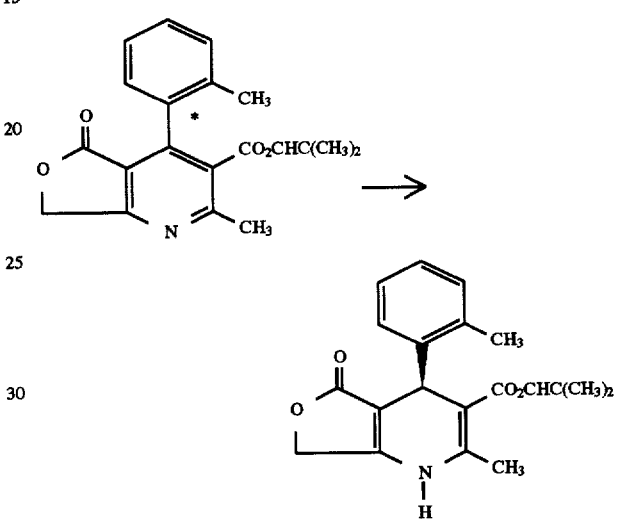

The procedure as described for Example 17 is followed. The current is 30 mA for 1.5 h.

The table below gives the enantiomer yields achieved in the Examples 1–19:

| Example No. | Enantiomer ratio | ee %* |
|---|---|---|
| 1 | 4:96 | 92 |
| 2 | 4:96 | 92 |
| 3 | 29.5:70.5 | 51 |
| 4 | 23:77 | 54 |
| 5 | 76.2:23.8 | 52.4 |
| 6 | 95:5 ($NO_2BF_4$); 97.2:2.8 ($NOBF_4$) | 90.6/94.4 |
| 7 | 94.3:5.7 | 88.6 |
| 8 | 6:94 | 88 |
| 9 | 4:6 (dioxane); 48:52 ($CHCl_3$) | 20/4 |
| 10 | 70.4:29.6 | 64.9 |
| 11 | 59:41 | 18 |
| 12 | 45:55 | 9.8 |
| 13 | 35:65 | 30 |
| 14 | 9:91 (version 1); 25.9:74.1 (version 2) | 83/48 |
| 15 | 16:48 | 69 |
| 16 | 3:2 | 20 |
| 17 | 90.2:9.8 | 85.6 |
| 18 | 61.3:38.7 | 23 |
| 19 | 46:54 | 11.8 |

*The ee for the reaction was calculated taking into account the ee of the starting material

I claim:
1. A process for the preparation of an optically active 1,4-dihydropyridine wherein the chiral C atom in the 4 position carries an ortho substituted aryl radical of the formula

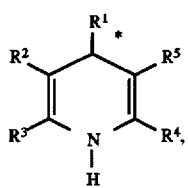
(I)

in which

R¹ represents an aryl radical of the formula

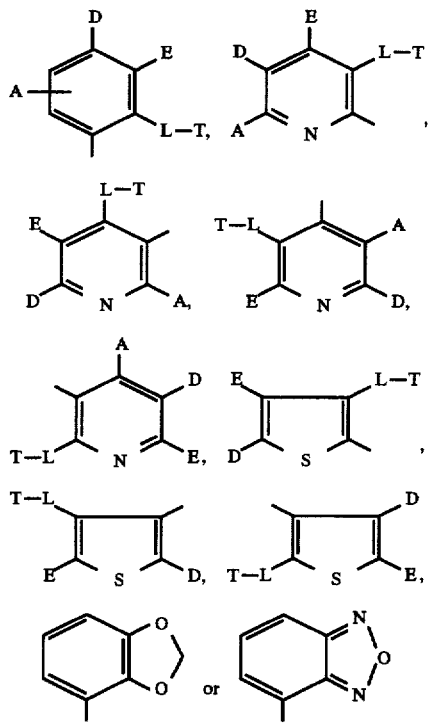

in which

A, D and E are identical or different and denote hydrogen, halogen, cyano, trifluoromethyl or denote straight-chain or branched alkyl or alkenyl having in each case up to 6 carbon atoms, each of which is optionally substituted by aryl having 6 to 10 carbon atoms, by a 5- to 7-membered saturated to unsaturated heterocycle having up to 3 hetero atoms selected from the group consisting of S, N and O or by straight-chain or branched alkoxycarbonyl having up to 8 carbon atoms or carboxyl, or denote a group of the formula —NR⁶R⁷, —OR⁸, —S(O)$_a$R⁹, —SR¹⁰ or —P(O)(OR¹¹)(OR¹²), in which R⁶, R⁷, R⁸ and R¹⁰ are identical or different and denote hydrogen, straight-chain or branched alkyl having up to 8 carbon atoms, benzyl, aryl having 6 to 10 carbon atoms or a 5- to 7-membered saturated or unsaturated heterocycle having up to 3 hetero atoms selected from the group consisting of S, N and O, a denotes a number 1 or 2, R⁹ denotes straight-chain or branched alkyl having up to 6 carbon atoms, benzyl, phenyl or tolyl, R¹¹ and R¹² are identical or different and denote hydrogen or straight-chain or branched alkyl having up to 6 carbon atoms, L denotes a direct bond, a sulphur or oxygen atom or a radical of the formula —NH or SO₂, T, depending on the definition of the substituent L, has one of the chemically meaningful meanings given above of A, D and/or E and is identical to or different from this, but in the cases L=bond or —SO₂ does not represent hydrogen, or denotes a radical of the formula —CHF₂, or D and E, in the directly adjacent case, or E and T, with inclusion of the aromatic double bond, in each case together form a 5- to 8-membered, partially unsaturated or unsaturated carbocycle or heterocycle having up to 3 hetero atoms selected from the group consisting of S, N and O, where the ring systems are optionally up to disubstituted identically or differently by halogen, hydroxyl, nitro, cyano, trifluoromethyl, by straight-chain or branched alkyl or alkoxy having in each case up to 6 carbon atoms, by aryl having 6 to 10 carbon atoms or by a 5- to 6-membered aromatic heterocycle having up to 3 hetero atoms selected from the group consisting of S, N and O, R² and R⁵ are identical or different and represent cyano, nitro, carboxyl or straight chain or branched alkoxycarbonyl having up to 6 carbon atoms which is optionally substituted by straight-chain or branched alkoxy or acyl having in each case up to 8 carbon atoms or by straight-chain or branched alkyl having up to 6 carbon atoms, which is optionally substituted by straight-chain or branched acyl having up to 4 carbon atoms, pyridyl, furanyl or by a group of the formula —NR¹³R¹⁴, in which R¹³ and R¹⁴ are identical or different and denote hydrogen, straight-chain or branched alkyl having up to 6 carbon atoms, aryl having 6 to 10 carbon atoms or benzyl, where the ring systems are optionally substituted by halogen, or alkoxycarbonyl is optionally substituted by a group of the formula —NR¹⁵R¹⁶, in which R¹⁵ and R¹⁶ have the meaning cited above of R¹³ and R¹⁴ and are identical to or different from these, or R² and/or R⁵ represent a radical of the formula —PO(OR¹⁷)(OR¹⁸), —SO₂R¹⁹ or —CO—NR²⁰R²¹, in which R¹⁷ and R¹⁸ have the meaning given above of R¹⁰ and R¹¹ and are identical to or different from these, or R¹⁷ and R¹⁸ together form a radical of the formula

R¹⁹ has the meaning given above of R⁹ and is identical to or different from this, R²⁰ and R²¹ are identical or different and denote hydrogen, straight-chain or branched alkyl having up to 6 carbon atoms or phenyl, R³ and R⁴ are identical or different and represent amino, cyano or straight-chain or branched alkinyl or alkyl having in each case up to 4 carbon atoms, each of which is optionally substituted by hydroxyl or by a group of the formula —(O—CO)$_b$—NR²²R²³, in which
b denotes a number 0 or 1,
R$^{22}$ and R$^{23}$ are identical or different and have the meaning given above of R$^6$ and R$^7$, or alkyl is optionally substituted by straight-chain or branched alkoxy having up to 6 carbon atoms which itself is optionally substituted by a group of the formula —NR$^{24}$R$^{25}$, in which
R$^{24}$ and R$^{25}$ have the meaning given above of R$^{13}$ and R$^{14}$ and are identical to or different from these, or R$^2$ and R$^3$, or R$^4$ and R$^5$, together form a radical of the formula $$X\diagdown\diagup Y$$

in which

X denotes an oxygen or sulphur atom or a group of the formula —NR$^{26}$ or —(CH$_2$)$_c$—,
in which
R$^{26}$ denotes hydrogen, phenyl or straight-chain or branched alkyl having up to 4 carbon atoms,
c denotes a number 1, 2 or 3,
and
Y denotes a group of the formula CO—, SO$_2$— or —SO, which comprises first converting by oxidation of the corresponding dihydropyridine which has a chiral C atom in the 4 position and is substituted by an ortho-substituted aryl or heteroaryl radical and which is present in the synperiplanar (sp) form of formula (Ia) or antiperiplanar (ap) form of formula (Ib) or its antipode in which
R$^2$, R$^3$, R$^4$, R$^5$, L and T have the meaning given above
and

—◯— includes the ortho-substituted aromatic ring systems cited above under the substituent R$^1$,
into an atropisomeric pyridine of the formulae (IIa) or (IIb)

(IIa)

(IIb)

in which
R$^2$, R$^3$, R$^4$, R$^5$, L, T and

—◯— have the meaning given above, and, in a second step, reducing the pyridines formed above back into the 1,4-dihydropyridine of formula (I), wherein either an inversion takes place to form the mirror-image isomer or a racemization takes place with partial retention to a differing extent.

2. The process according to claim 1, wherein the dihydropyridine prepared is one in which
R$^1$ represents a radical of the formula in which
A, D and E are identical or different and denote hydrogen, fluorine, chlorine, bromine, cyano, trifluoromethyl or straight-chain or branched alkyl or alkenyl having in each case up to 5 carbon atoms, each of which is optionally substituted by phenyl, naphthyl, pyridyl or by straight-chain or branched alkoxycarbonyl having up to 6 carbon atoms or carboxyl, or denote a group of the formula —NR$^6$R$^7$, —OR$^8$, —S(O)$_a$R$^9$, —SR$^{10}$ or —P(O)(OR$^{11}$)(OR$^{12}$),
in which
R$^6$, R$^7$, R$^8$ and R$^{10}$ are identical or different and denote hydrogen, straight-chain or branched alkyl having up to 6 carbon atoms, benzyl, phenyl, pyridyl, furyl or thienyl,
a denotes a number 1 or 2,
R$^9$ denotes straight-chain or branched alkyl having up to 4 carbon atoms, benzyl, phenyl or tolyl, $R^{11}$ and $R^{12}$ are identical or different and denote hydrogen or straight-chain or branched alkyl having up to 3 carbon atoms, L denotes a direct bond, a sulphur atom or oxygen atom or a radical of the formula —NH or $SO_2$, T, depending on the definition of the substituent L, has one of the chemically meaningful meanings given above of A, D and/or E and is identical to or different from this, but in the cases L=bond or —$SO_2$ does not represent hydrogen, or denotes a radical of the formula —$CHF_2$, or D and E, in the directly adjacent case, or E and T, with inclusion of the aromatic double bond, in each case together form a fused cyclopentenyl, cyclohexenyl, cycloheptenyl, cyclohexadienyl, cycloheptadienyl or pyridyl ring, where the ring systems are optionally substituted by phenyl, thienyl, straight-chain or branched alkyl having up to 4 carbon atoms or pyridyl, $R^2$ and $R^5$ are identical or different and represent cyano, nitro, carboxyl or straight-chain or branched alkoxy-carbonyl having up to 5-carbon atoms which is optionally substituted by straight-chain or branched alkoxy or acyl having in each case up to 6 carbon atoms or by straight-chain or branched alkyl having up to 5 carbon atoms, which itself is optionally substituted by straight-chain or branched acyl having up to 3 carbon atoms, pyridiyl, furanyl or by a group of the formula —$NR^{13}R^{14}$, in which $R^{13}$ and $R^{14}$ are identical or different and denote hydrogen, straight-chain or branched alkyl having up to 5 carbon atoms, phenyl, naphthyl or benzyl, where the ring systems are optionally substituted by fluorine, chlorine or bromine, or alkoxycarbonyl is optionally substituted by a group of the formula —$NR^{15}R^{16}$, in which $R^{15}$ and $R^{16}$ have the meaning cited above of $R^{13}$ and $R^{14}$ and are identical to or different from this, or $R^2$ and/or $R^5$ represent a radical of the formula —PO($OR^{17}$)($OR^{18}$), —$SO_2R^{19}$ or —CO—$NR^{20}R^{21}$, in which $R^{17}$ and $R^{18}$ have the meaning given above of $R^{10}$ and $R^{11}$ and are identical to or different from these, or $R^{17}$ and $R^{18}$ together form a radical of the formula

$R^{19}$ has the meaning given above of $R^9$ and is identical to or different from this, $R^{20}$ and $R^{21}$ are identical or different and denote hydrogen, straight-chain or branched alkyl having up to 4 carbon atoms, or phenyl, $R^3$ and $R^4$ are identical or different and represent amino, cyano or straight-chain or branched alkinyl or alkyl having in each case up to 3 carbon atoms, which is optionally substituted by hydroxyl or by a group of the formula —(O—CO)$_b$—$NR^{22}R^{23}$, in which b denotes a number 0 or 1, $R^{22}$ and $R^{23}$ are identical or different and have the meaning given above of $R^6$ and $R^7$, or alkyl is optionally substituted by straight-chain or branched alkoxy having up to 4 carbon atoms which itself is optionally substituted by group of the formula —$NR^{24}R^{25}$, in which $R^{24}$ and $R^{25}$ have the meaning given above of $R^{13}$ and $R^{14}$ and are identical to or different from this, or $R^2$ and $R^3$, or $R^4$ and $R^5$, together form a radical of the formula

in which

X denotes an oxygen atom or sulphur atom or a group of the formula —$NR^{26}$ or —$(CH_2)_c$, in which $R^{26}$ denotes hydrogen, phenyl or straight-chain or branched alkyl having up to 3 carbon atoms, c denotes a number 1, 2 or 3, and Y denotes a group of the formula CO—, $SO_2$— or —SO.

3. The process according to claim 1, wherein the dihydropyridine prepared is one in which $R^1$ represents a radical of the formula

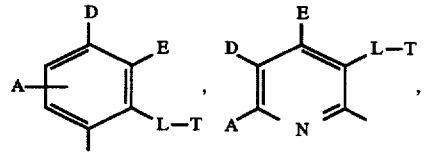

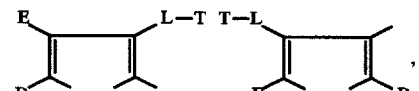

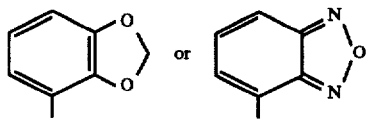

in which

A, D and E are identical or different and denote hydrogen, fluorine, chlorine, bromine, cyano, trifluoromethyl or straight-chain or branched alkyl or alkenyl having in each case up to 4 carbon atoms each of which is optionally substituted by phenyl, naphthyl, pyridyl or by straight-chain or branched alkoxycarbonyl having up to 5 carbon atoms or carboxyl, or denote a group of the formula —$NR^6R^7$, —$OR^8$, —$S(O)_aR^9$, —$SR^{10}$ or —$P(O)(OR^{11})(OR^{12})$, in which $R^6, R^7, R^8$ or $R^{10}$ are identical or different and denote hydrogen, straight-chain or branched alkyl having up to 4 carbon atoms, benzyl, phenyl, pyridyl or furyl, a denotes a number 1 or 2, $R^9$ denotes methyl, benzyl, phenyl or tolyl, $R^{11}$ and $R^{12}$ are identical or different and denote hydrogen or straight-chain or branched alkyl having up to 3 carbon atoms, L denotes a direct bond, a sulphur atom or oxygen atom or a radical of the formula —NH or $SO_2$, T, depending on the definition of the substituent L, has one of the chemically meaningful meanings given above of A, D and/or E and is identical to or different from this, but in the cases L=bond or —$SO_2$ does not represent hydrogen, or denotes a radical of the formula —$CHF_2$, or D and E, in the directly adjacent case, or E and T, with inclusion of the aromatic double bond, in each case together form a fused cyclopentenyl, cyclohexenyl, cycloheptenyl, cyclohexadienyl, cycloheptadienyl or pyridyl ring, where the ring systems are optionally substituted by phenyl, thienyl, straight-chain or branched alkyl having up to 3 carbon atoms or pyridyl, $R^2$ and $R^5$ are identical or different and denote cyano, nitro, carboxyl or straight-chain or branched alkoxycarbonyl having up to 4 carbon atoms which is optionally substituted by straight-chain or branched alkoxy or acyl having in each case up to 3 carbon atoms or by straight-chain or branched alkyl having up to 3 carbon atoms, which can itself be substituted by straight-chain or branched acyl having up to 3 carbon atoms, pyridyl, furanyl or by a group of the formula —$NR^{13}R^{14}$, in which $R^{13}$ and $R^{14}$ are identical or different and denote hydrogen, straight-chain or branched alkyl having up to 4 carbon atoms, or $R^2$ and/or $R^5$ represent a radical of the formula —$PO(OR^{17})(OR^{18})$, —$SO_2R^{19}$ or —$CO-NR^{20}R^{21}$, in which $R^{17}$ and $R^{18}$ have the meaning given above of $R^{10}$ and $R^{11}$ and are identical to or different from these, or $R^{17}$ and $R^{18}$ together form a radical of the formula

$R^{19}$ has the meaning given above of $R^9$ and is identical to or different from this, $R^{20}$ and $R^{21}$ are identical or different and denote hydrogen, straight-chain or branched alkyl having up to 3 carbon atoms, $R^3$ and $R^4$ are identical or different and represent amino, cyano or straight-chain or branched alkinyl or alkyl having in each case up to 3 carbon atoms, which is optionally substituted by hydroxyl or by a group of the formula —$(O-CO)_b-NR^{22}R^{23}$, in which b denotes a number 0 or 1, $R^{22}$ and $R^{23}$ are identical or different and have the meaning given above of $R^6$ and $R^7$, or alkyl is optionally substituted by straight-chain or branched alkoxy having up to 3 carbon atoms which itself is optionally substituted by a group of the formula —$NR^{24}R^{25}$, in which $R^{24}$ and $R^{25}$ have the meaning given above of $R^{13}$ and $R^{14}$ and are identical to or different from this, or $R^2$ and $R^3$, or $R^4$ and $R^5$, together form a radical of the formula

in which

X denotes an oxygen atom or sulphur atom or a group of the formula —$NR^{26}$ or —$(CH_2)_c$, in which $R^{26}$ denotes hydrogen, phenyl or straight-chain or branched alkyl having up to 3 carbon atoms, c denotes a number 1, 2 or 3, and Y denotes the CO group.

4. The process according to claim 1, where the oxidation step is carried out by anodic oxidation or an oxidizing agent selected from the group consisting of NO, $HNO_3$, $NOBF_4$ or $NO_2BF_4$ is employed.

5. The process according to claim 1, wherein the reduction step is carried out by cathodic reduction where the electrolysis cell comprises a cathode, an anode and a reference cell in solution or a reducting agent.

6. The process according to claim 5, wherein the cathode is graphite, carbon, Pt, Pd, Pb, Cd, Ni or a mercury pool electrode and the anode is carbon, graphite or Pd.

7. The process according to claim 5, wherein the cathodic reduction is carried out under voltage control between −0.5 V and −2.5 V, or under current control with currents of 5 mA to 1 A.

* * * * *

UNITED STATES PATENT AND TRADEMARK OFFICE
CERTIFICATE OF CORRECTION

PATENT NO. : 5,708,177
DATED : January 13, 1998
INVENTOR(S) : Straub, Alexander

It is certified that error appears in the above-identified patent and that said Letters Patent is hereby corrected as shown below:

Col. 19, line 53  Delete " $-S(O)_2R^9$ " and substitute -- $-S(O)_aR^9$ --

Signed and Sealed this

Tenth Day of November 1998

Attest:

BRUCE LEHMAN

Attesting Officer        Commissioner of Patents and Trademarks